United States Patent
Markus

(10) Patent No.: US 8,790,332 B2
(45) Date of Patent: Jul. 29, 2014

(54) LASER APPLICATOR

(75) Inventor: Kai Ulf Markus, Eschweiler (DE)

(73) Assignee: VIMECON GmbH, Herzogenrath (DE)

(*) Notice: Subject to any disclaimer, the term of this patent is extended or adjusted under 35 U.S.C. 154(b) by 286 days.

(21) Appl. No.: 13/130,106

(22) PCT Filed: Jul. 29, 2009

(86) PCT No.: PCT/EP2009/059818
§ 371 (c)(1),
(2), (4) Date: May 19, 2011

(87) PCT Pub. No.: WO2010/057689
PCT Pub. Date: May 27, 2010

(65) Prior Publication Data
US 2011/0230871 A1    Sep. 22, 2011

(30) Foreign Application Priority Data
Nov. 20, 2008 (DE) .......................... 10 2008 058 148

(51) Int. Cl.
*A61B 18/18* (2006.01)
(52) U.S. Cl.
USPC .................................. 606/15; 606/13; 606/16
(58) Field of Classification Search
CPC .............................................. A61B 2018/2272
USPC ................... 606/7, 12–16; 600/433, 435, 478
See application file for complete search history.

(56) References Cited

U.S. PATENT DOCUMENTS

| | | | |
|---|---|---|---|
| 5,025,778 A | 6/1991 | Silverstein et al. | |
| 5,042,980 A * | 8/1991 | Baker et al. | 606/7 |
| 5,248,311 A * | 9/1993 | Black et al. | 606/15 |
| 5,405,369 A * | 4/1995 | Selman et al. | 607/88 |
| 6,117,128 A * | 9/2000 | Gregory | 606/7 |
| 6,343,174 B1* | 1/2002 | Neuberger | 385/123 |
| 6,676,656 B2 | 1/2004 | Sinofsky | |
| 6,873,868 B2 | 3/2005 | Furnish | |
| 2003/0199736 A1 | 10/2003 | Christopher | |
| 2004/0143286 A1* | 7/2004 | Johnson et al. | 606/194 |
| 2005/0273090 A1 | 12/2005 | Nieman et al. | |
| 2005/0288654 A1 | 12/2005 | Nieman et al. | |
| 2006/0084960 A1 | 4/2006 | Mester et al. | |
| 2009/0275931 A1 | 11/2009 | Markus | |

FOREIGN PATENT DOCUMENTS

| | | |
|---|---|---|
| DE | 102006039471 B3 | 3/2008 |
| WO | 2004078045 A1 | 9/2004 |
| WO | 2005120379 A2 | 12/2005 |
| WO | 2007035456 A1 | 3/2007 |
| WO | 2007118745 A1 | 10/2007 |

* cited by examiner

*Primary Examiner* — Gary Jackson
*Assistant Examiner* — Nathan J Jenness
(74) *Attorney, Agent, or Firm* — Fay Sharpe LLP

(57) ABSTRACT

The laser applicator includes a catheter (10) having a proximal section (10a), a midsection (10b) and a distal end section (10c). It contains a light guide, the light of which is output in a decoupling portion (40). The light guide runs in a longitudinal groove on the outside of a catheter body. While the light guide (20) is continuous, the catheter is composed of catheter bodies, which are joined together at a catheter splice site (37).

15 Claims, 2 Drawing Sheets

LASER APPLICATOR

BACKGROUND

The invention refers to a laser applicator with an elongate catheter including at least one circumferentially closed lumen and with a light guide extending along the catheter, which light guide comprises a decoupling portion in a distal end section of the catheter.

Such a laser applicator is described in US 2009/0275932 (Vimecon), the disclosure of which is incorporated into the present application by reference. The known laser applicator comprises an elongate flexible catheter including a light guide. The distal end section is formed into a lariat-like shape whose plane extends transversely to the main portion of the catheter. Laser radiation is input into the light guide at the proximal end. A decoupling portion exists at the distal end of the catheter, where the energy is coupled laterally out of the light guide and exits from the catheter.

In particular, the laser applicator serves for the treatment of atrial fibrillation and other types of cardiac arrhythmia. It can be used to cauterize cardiac tissue by converting light energy into thermal energy. The laser radiation exiting the light guide heats the surrounding tissue to values above 60° C., resulting in the denaturation of proteins and the formation of an electrically inactive scar.

DE 10 2006 039 471 B3 describes a laser applicator comprising a catheter with a light guide. In a distal end section of the catheter, the cladding of the light guide has a cutout from which light exits laterally from the light guide. While the intact cladding of the light guide effects total internal reflection so that the light energy is transported in the longitudinal direction of the light guide, the cutouts at the border of the light guide core cause refraction so that light energy is coupled out.

The present invention addresses the structural design of a laser applicator. It is an object of the invention to provide a laser applicator that is simple and economical to manufacture and is thus particularly well suited for industrial production.

SUMMARY

According to one aspect of the laser applicator, the decoupling portion of the light guide extends in a groove on the outer side of the catheter, which groove is filled with a translucent material.

According to another aspect, at least the decoupling portion of the light guide is set into a laterally open groove in the catheter. This makes it possible to work the light guide before inserting it into the catheter, in particular to remove parts of the cladding of the light guide in the decoupling portion. The light guide thus worked may then be placed laterally in the longitudinal groove of the catheter. Thereafter, it is fixed using a translucent material, in particular a corresponding adhesive. Attaching the light guide in an outer groove of the catheter causes a significant simplification of the laser applicator manufacturing process.

Generally, the groove on the outer side of the catheter may have any optional cross section, i.e. rectangular or semicircular, for instance. In a preferred embodiment of the invention, the groove is V-shaped and has flanks provided with a reflective layer. Radiation energy laterally exiting from the light guide and scattered in the surrounding translucent material, is reflected by the reflective layers, whereby a bundling and focusing is effected. The V-shape of the groove should not be understood literally. The angle portion where the two reflective layers meet may be rounded. A parabolic groove should also be understood to be covered by the term "V-shaped". It is important that the groove flanks diverge outward so that the reflective layer bundles scattered radiation and focuses the same at a point outside the catheter cross section. Scattered radiation inside the translucent material can be caused by providing the translucent material with distributed dispersing particles.

Preferably, in a midsection of the catheter, the light guide is also accommodated in a groove on the outer side of the catheter. In particular, the whole length of the light guide may be accommodated in a groove on the outer side of the catheter. Thereby, it is avoided that the light guide has to be drawn into a catheter lumen. Rather, the light guide can be treated separately before it is placed into the catheter. Placing the fiber into the catheter is done from outside by setting it into the groove open to the outer side.

In a preferred embodiment of the invention, the midsection and the distal end section of the catheter are made from two separate catheter components joined at a catheter splice site. The light guide extends integrally across the midsection and the distal end section. While the catheter is composed of two catheter components, the light guide is integral. Thereby, energy losses are minimized.

A preferred embodiment of the invention provides that the catheter comprises at least one cooling channel provided with outlet bores in the distal end section. Thus, cooling liquid can be transported directly to the body tissue thermally treated. Preferably, two cooling channels are provided that are arranged at both sides of the light guide and whose outlet bores are directed towards each other. Here, two cooling flows are combined at the treatment site of the body tissue, whereby an effective local cooling is achieved using only little cooling medium.

For the purpose of smoothing the outer side of the catheter, the distal end section may be provided with a translucent covering hose and the midsection may be provided with an opaque covering hose, wherein the two covering hoses are joined at a hose splice site.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

In the Figures.

DETAILED DESCRIPTION

Figure 1:
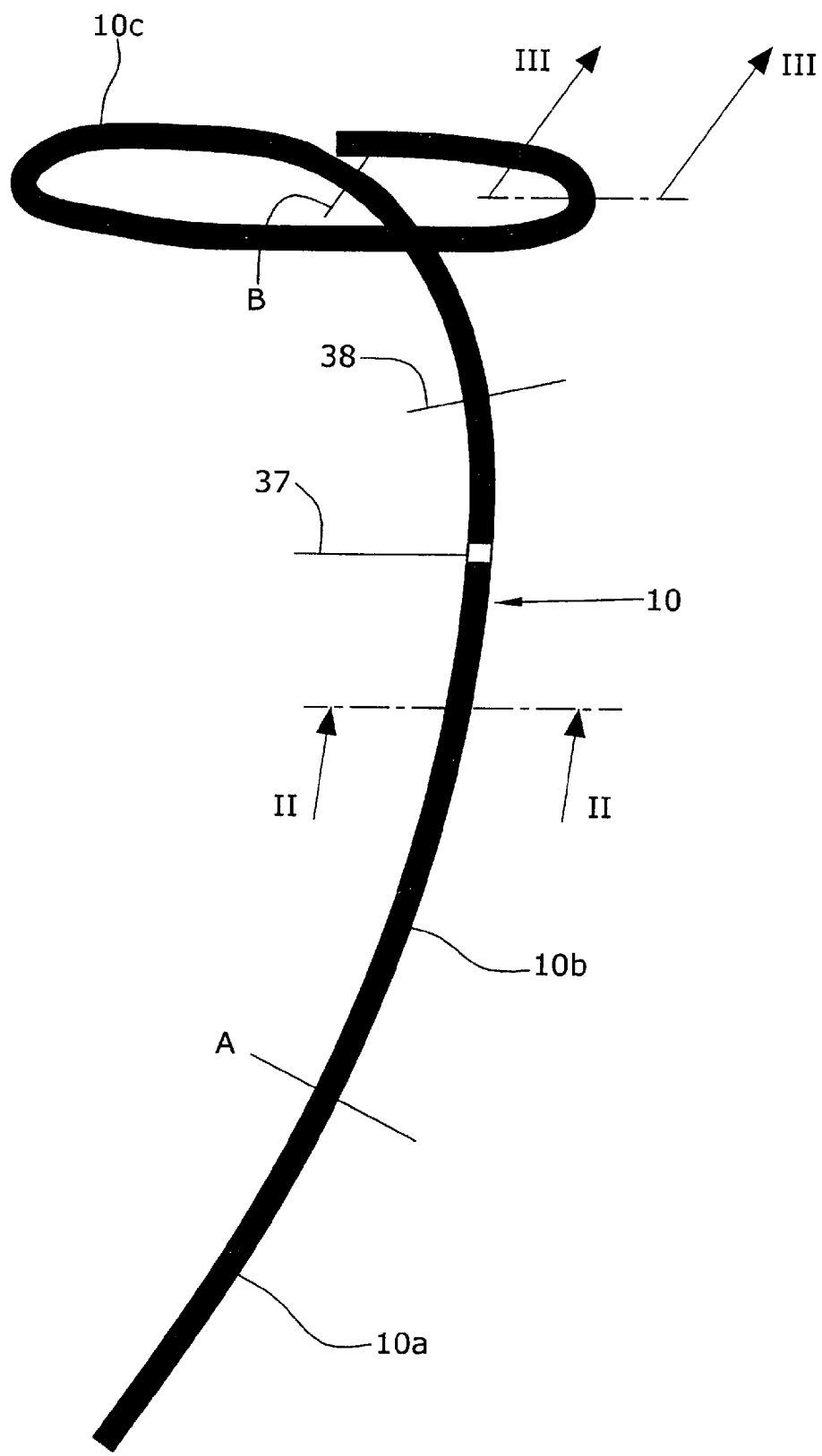
FIG. 1 is a schematic illustration of the general structure of the light guide.

The laser applicator comprises a catheter 10 in the form of an elongate strand. The catheter has one or a plurality of lumens. It is preformed in the manner illustrated in FIG. 1 and is composed of a proximal section 10a, a midsection 10b and a distal end section 10c. Whereas the sections 10a and 10b extend substantially linearly, the distal end section 10c is formed into a loop shaped as a circle open at one point. The plane of the loop is transverse, in particular at a right angle, with respect to the longitudinal direction of the midsection

10b. It is dimensioned such that it contacts the wall of a blood vessel from inside with slight pressure. The outer diameter of the loop is about 20-40 mm.

The position A indicates the transition from the proximal section 10a to the midsection 10b. The position B indicates the transition from the midsection 10b to the distal end section 10c.

Figure 2:
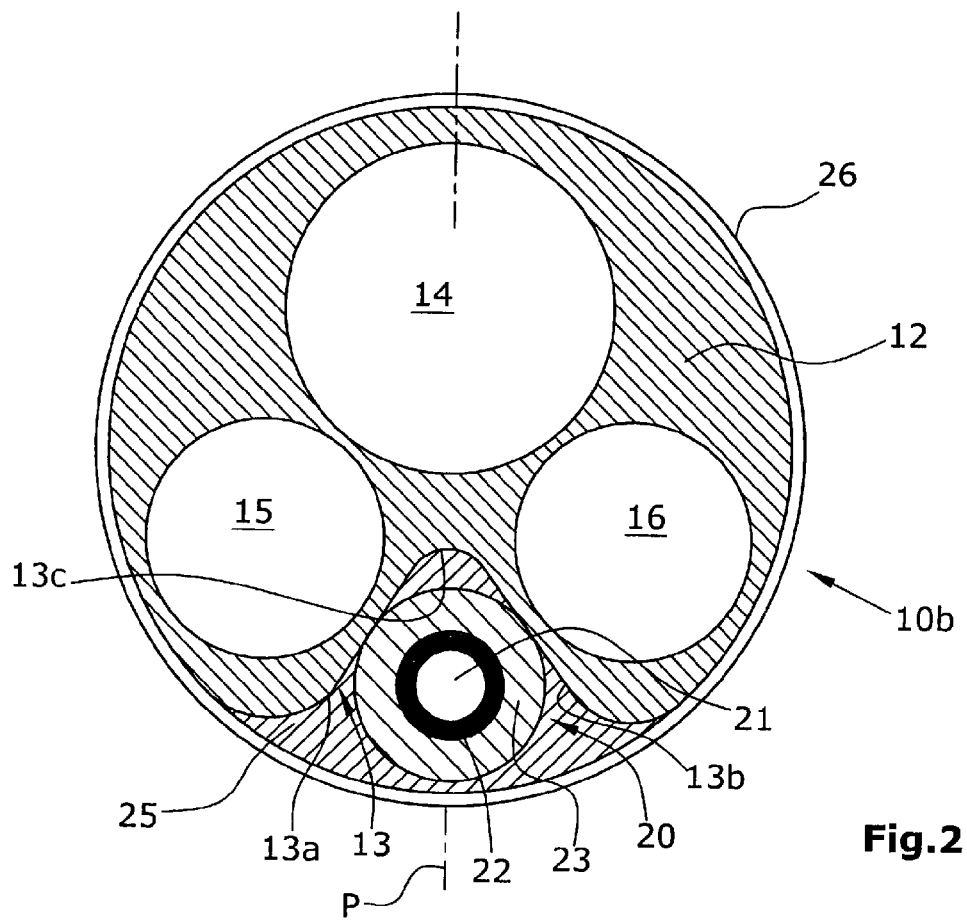
FIG. 2 is a cross section along line II-II in the midsection of the catheter and FIG. 3 is a cross section along line in the distal end section of the catheter.

FIG. 2 illustrates a cross section through the catheter in the midsection 10b. The catheter has an integral elongate catheter body 12 with a diameter of 2-3 mm which is substantially circular in cross section and is provided with a longitudinally extending, substantially V-shaped groove 13. The groove 13 has two flanks 13a, 13b diverging outward that are connected by an arcuate base 13c. The groove extends up to near the longitudinal center axis of the catheter body 12.

The catheter body 12 has a lumen 14 for a forming wire. The lumen 14 is arranged diametrically opposite the groove 13. Further, two longitudinally extending cooling channels 15, 16 are provided that extend over the entire length of the catheter and are arranged symmetrically with respect to the longitudinal centre plane P that forms a symmetry plane and passes through the center of the lumen 14 and the center plane of the groove 13. The catheter body 12 is an elastomeric profile strand with a uniform profile all over its length.

A light guide 20 is set into the groove 13 from outside. The light guide is composed of a core 21 formed by a glass fiber, as well as of a cladding 22 surrounding the core 21, the material of the cladding having a higher refraction index than the core 21. The cladding 22 is surrounded by a protective sheath 23 that acts as an anti-breaking device. The entire light guide 20 has a diameter such that it fits into the groove 13 without protruding beyond the circular contour of the catheter.

The light guide 20 is fixed in the groove 13 by means of an adhesive 25 filling the entire groove and having an outer surface corresponding to the circular contour of the catheter body. The adhesive 25 is impermeable to the radiation. On the outside, the catheter is sheathed in an opaque covering hose 26.

Figure 3:
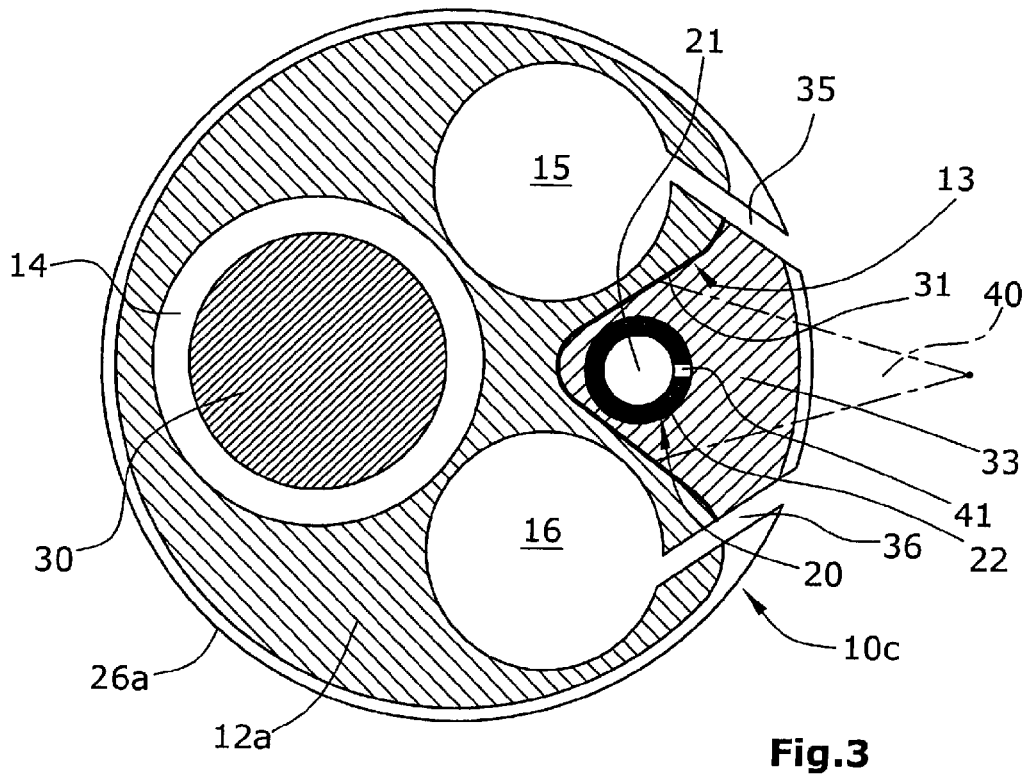

In the distal end section 10c, the catheter has the cross section illustrated in FIG. 3. It comprises a catheter body 12a that has the same profile as the catheter body 12 of the midsection. A forming wire 30 is situated in the lumen 14, which wire gives the distal end section 10c the loop shape illustrated in FIG. 1, while, however, being resilient and being adapted to be extended. In the distal end section 10c, the protective sheath 23 is removed from the light guide 20. Here, the groove 13 is provided with a reflective layer 31 that covers the flanks of the groove and the base 13c. In the distal end section, the light guide 20 only comprises the core 21 and the cladding 22. It is embedded in the groove, with the groove 13 being filled with a translucent material 33. This material is an adhesive containing light-scattering particles.

In the distal end section the catheter is also provided with a covering hose 26a which, however, is translucent in this section.

In the distal end section, the cooling channels 15, 16 are provided with outlet bores 35, 36 that converge towards each other and eject cooling jets outward. The outlet bores 35, 36 extend under an acute angle with respect to each other.

They cause the cooling jets to impinge on the target area of the heat radiation. The outlet bores 35, 36 have corresponding openings in the covering hose. In the decoupling portion 40 (FIG. 1), where the radiation is coupled out from the light guide 20, the cladding 22 of the light guide is provided with openings 41 through which the radiation is coupled out from the core 21. The decoupling portion 40 is directed radially outward with respect to the loop of the distal end section. The symmetry plane P (FIG. 2) is on the plane of the loop.

The core 21 of the light guide 20 and the cladding 22 are continuous over the entire length of the catheter 10 so that the glass fiber of the light guide is not interrupted. The catheter bodies 12 and 12a are joined at a catheter splice site 37. The covering hoses 26 and 26a are joined at a hose splice site 38 arranged at a distance, in the present instance distally, from the catheter splice site 37.

When the laser applicator is manufactured, first, the catheter bodies 12, 12a are cut from the same hose profile. The catheter body 12a is then provided with the reflective layer 31. The same is a metal layer formed by sputtering or vapor deposition.

The light guide 20 is first worked outside the catheter by removing the protective sheath 23 from sections thereof. Openings 41 in the form of small bores are formed in this decoupling portion by laser machining. The light guide thus prepared is set into the lateral groove 13 of the catheter body 12 and is then fixed using the adhesive 25. Then the catheter body 12a is joined with the catheter body 12 at the catheter splice site 37, the bodies fitting precisely. Finally, the decoupling portion of the light guide 20 is set into the lateral groove of the catheter body 12a and the groove is filled with the material 33.

Finally, the covering hoses 26 and 26a are applied on the respective catheter sections.

The invention offers the advantage that only the catheter bodies are joined by splicing and the covering hoses are also spliced in the same manner. In contrast thereto, the light guide is continuous, being machined only in the decoupling portion. The laser applicator has low energy losses and it is adapted to apply a high energy concentration in the target area.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A laser applicator comprising an elongate catheter including at least one circumferentially closed lumen and a light guide extending along the catheter, said light guide having a decoupling portion in a distal end section of the catheter, the decoupling portion of the light guide extending in a groove in an outer side of the catheter, wherein the groove is filled with a translucent material; and
   two cooling channels, arranged on opposing sides of the light guide, the cooling channels including outlet bores convergently directed towards each other in the distal end section.

2. The laser applicator of claim 1, wherein in a midsection of the catheter, the light guide also extends in a groove on the outer side of the catheter.

3. The laser applicator of claim 2, wherein the catheter is formed by two separate catheter components, in the midsection and the distal end section, joined at a catheter splice site and the light guide extends integrally along the midsection and the distal end section.

4. The laser applicator of claim 3, wherein both catheter components have the same profile.

5. The laser applicator of claim 2, wherein the light guide has a protective sheath on the midsection and is protective sheath free in the decoupling portion.

6. The laser applicator of claim 2, further including a translucent covering hose on the distal end section and an opaque covering hose on the midsection, said two covering hoses being joined at a hose splice site.

7. The laser applicator of claim 1, wherein the light guide comprises a light-guiding core and a cladding surrounding the core, the cladding being provided with openings.

8. The laser applicator of claim 1, wherein the outlet bores of both cooling channels extend at an acute angle with respect to each other.

9. The laser applicator of claim 1, wherein the catheter is covered with a covering hose at least in the distal end section.

10. The laser applicator of claim 1, wherein the catheter includes a forming wire that resiliently forms the distal end section in the manner of a circular loop.

11. The laser applicator of claim 10, wherein the forming wire has a wire axis and the light guide has a light guide axis, and the wire axis and the light guide axis lie in a diametrical plane of the catheter cross section, the forming wire being arranged on the inside in the circular loop.

12. The laser applicator of claim 1, wherein the translucent material fixes the light guide in the groove and decouples light laterally.

13. A laser applicator, comprising:
an elongated flexible catheter which defines at least one interior lumen and an external groove, the elongated catheter having a proximal end and a distal end;
a light guide disposed in the groove and extending from the proximal end to the distal end, the light guide including a light guiding core surrounded by cladding, the cladding having a plurality of openings adjacent the distal end;
a material anchoring the light guide in and filling the groove, the material being translucent adjacent the distal end; and
cooling channels defined in the catheter adjacent the groove, the cooling channels having outlet bores adjacent the distal end, wherein the bores converge in front of the light guide.

14. The laser applicator of claim 13, wherein the groove has an elongated reflective layer lining the groove adjacent the distal end such that light emitted through the openings towards the groove is reflected.

15. The laser applicator of claim 13, further including a protective covering which surrounds the catheter, the light guide and the material, the covering being translucent adjacent the distal end.

* * * * *